United States Patent [19]

Speck

[11] Patent Number: 5,637,452
[45] Date of Patent: Jun. 10, 1997

[54] KIT FOR AN INITIAL SCREEN FOR ABNORMAL PLATELET CONDITION COMPRISING PROPYL GALLATE OR TANNIN AND A METAL ION

[75] Inventor: Roy E. Speck, Indianapolis, Ind.

[73] Assignee: Analytical Control Systems, Inc., Fishers, Ind.

[21] Appl. No.: 477,694

[22] Filed: Jun. 7, 1995

Related U.S. Application Data

[62] Division of Ser. No. 390,273, Feb. 16, 1995, Pat. No. 5,569,590, which is a continuation of Ser. No. 955,679, Oct. 2, 1992, abandoned.

[51] Int. Cl.$^6$ .................. C12Q 1/00; C12Q 1/56; G01N 33/86
[52] U.S. Cl. .................. 435/4; 435/13; 436/69
[58] Field of Search .................. 435/4, 13, 2; 436/69

[56] References Cited

U.S. PATENT DOCUMENTS

| | | | |
|---|---|---|---|
| 3,486,981 | 12/1969 | Speck | 195/99 |
| 4,455,377 | 6/1984 | Finnerty et al. | 436/69 |
| 4,666,831 | 5/1987 | Janoff et al. | 435/13 |
| 4,732,860 | 3/1988 | Bartl et al. | 436/34 |
| 5,039,617 | 8/1991 | McDonald et al. | 436/69 |
| 5,055,412 | 10/1991 | Proksch | 436/69 |
| 5,215,888 | 6/1993 | Shaltiel et al. | 435/15 |

FOREIGN PATENT DOCUMENTS

| | | |
|---|---|---|
| 2915310A | 10/1980 | Germany . |
| 9011368 | 10/1990 | WIPO . |
| PCT/US91/ 02580 | 10/1991 | WIPO . |

OTHER PUBLICATIONS

A. Girolami et al., "Failure of Ellagic Acid to Affect Platelet Aggregation in Normal and in Factor XII Deficient Plasma", *Blut*, 31, 1975, pp. 107–112.

R. E. Speck, "Accurate Assays for Platelet Factor 3", *American Clinical Laboratory*, 12(9), 1993, pp. 16–18.

M. H. Kroll et al., "Biochemical Mechanisms of Platelet Activation", *Blood*, 74(4), 1989, pp. 1181–1195.

E.W. Salzman et al., "Effect of Heparin and Heparin Fractions on Platelet Aggregation", *Journal of Clinical Investigation*, 65, 1980, pp. 64–73.

J.D. Sweeney et al., "The Effect of the Platelet Count on the Aggregation Response and Adenosine Triphosphate Release in an Impedance Lumi-Aggregometer", *American Journal of Clinical Pathology*, 89, 1988, pp. 655–659.

J.D. Sweeney et al., "Ristocetin–Induced Platelet Aggregate Formation and Adherence to the Probe of an Impedance Aggregometer", *American Journal of Clinical Pathology*, 93, 1990, pp. 548–551.

C.E. Isenhart, "Platelet Aggregation Studies for the Diagnosis of Heparin–Induced Thrombocytopenia", *American Journal of Clinical Pathology*, 1993, pp. 324–330.

Y.S. Arkel, "Evaluation of Platelet Aggregation in Disorders of Hemostasis", *Medical Clinics of North America*, 60, 1976, pp. 881–911.

R.M. Hardisty et al., "The Kaolin Clotting Time of Platelet Rich Plasma: A Test of Platelet Factor 3 Availability", *British Journal of Haemotology*, 11, 1965, pp. 258–268.

E.J. Bowie, "Standardization of Platelets in the Thromboplastin Generation Test", *The American Journal of Clinical Pathology*, 44, 1965, pp. 673–677.

R.M. Hardisty et al., "Platelet Aggregation and the Availability of Platelet Factor 3", *British Journal of Haematology*, 12, 1966, pp. 764–776.

H. Sandberg et al., "A Highly Sensitive Assay of Platelet Factor 3 Using a Chromogenic Substrate", *Thrombosis Research*, 14, 1979, pp. 113–124.

P. E. Bock et al., "Activation of Intrinsic Blood Coagulation by Ellagic Acid: Insoluble Ellagic Acid–Metal Ion Complexes Are the Activating Species", *Biochemistry*, 20, 1981, pp. 7258–7266.

O.D. Ratnoff et al., "Activation of Hageman Factor by solutions of Ellagic Acid", *The Journal of Laboratory and Clinical Medicine*, 63, 1964, pp. 359–377.

V. Dayton et al., "Laboratory Diagnosis of Lupus Anticoagulant: Comparison of Three Methods of Antibody Neutralization", *Laboratory Medicie*, 1990, pp. 30–32.

T. Exner et al., "A Sensitive Test Demonstrating Lupus Anticoagulant and its Behavioral Patterns", *British Journal of Hematology*, 40, 1978, pp. 143–151.

D.A. Triplett et al., "Laboratory Diagnosis of Lupus Inhibitors: A Comparison of the Tissue Thromboplastin Inhibition Procedure with a New Platelet Neutralization Procedure", *American Journal of Clinical Pathology*, 79, 1983, pp. 678–682.

J. Aznar et al., "Effects of Contact Factor (Factor XII+Factor XI) on Aggregation of Platelets", *Haemostasis*, 3, 1974, pp. 20–30.

G. Rouser et al., "Phospholipid Structure and Thromboplastic Activity", *Biochimica Et Biophysica Acta*, 28, 1958, pp. 71–80.

R. G. Mason et al., "Some Effects of a Microcrystalline Collagen Preparation on Blood", *Hemostasis*, 3, 1974, pp. 31–45.

(List continued on next page.)

Primary Examiner—David M. Naff
Assistant Examiner—S. Saucier
Attorney, Agent, or Firm—Kenyon & Kenyon

[57] ABSTRACT

Described is a novel screening method for detecting an abnormal platelet condition in blood, and a kit for use in such a method. An initial screen for an abnormal platelet condition in blood applies to a non-interfering test surface a platelet rich plasma specimen from the blood and an aqueous reagent including a hydroxy-substituted aromatic compound such as elagic acid, tannin or preferably propyl gallate and a metal ion such as $Ni^{2+}$, $Co^{2+}$, $Fe^{3+}$, $Cu^+$ or $Cu^{2+}$ in concentrations sufficient to cause platelet aggregation in a normal platelet rich plasma sample upon agitation, lightly agitating the platelet rich plasma specimen in contact with the reagent, and visually detecting for the presence of platelet aggregates in the specimen.

16 Claims, No Drawings

OTHER PUBLICATIONS

A. P. Bode et al., "Analysis of Platelet Factor 3 in Platelet Concentrate Stored for Transfusion", *Vox Sanguinis*, 51, 1986, pp. 299–305.

Hervig et al., "Thrombin–Induced Serotonin Release as an in vitro Indicator of the Functional Integrity of Stored Platelets", Chin. Chem., vol. 36, No. 1, pp. 28–31 (1990).

Ramanathan et al., "Correlation Between Bleeding Times and Platelet Counts in Women With Preeclampsia Undergoing Cesarean Section", Anesthesiology, vol. 71, pp. 188–191 (1989).

Mitchell et al., "Platelet Clumping in vitro", Brit. J. Haemat., vol. 10, pp. 78–93 (1964).

Ardlie et al., "Adenosine Diphosphate–Induce Platelet Aggregation in Suspension of Washed Rabbit Platelets", Brit. J. of Haemat., vol. 19, pp. 7–17 (1970).

Born et al., "The Aggregation of Blood Platelets", J. Physiol., vol. 168, pp. 178–195 (1963).

Kinlough–Rathbone et al., "The Effect of Glucose on Adenosine Diphosphate–Induced Platelet Aggregation", J. Lab. Clin. Med., vol. 75, No. 5, pp. 780–787 (1970).

Brinkhous et al., "Macroscopic Studies of Platelet Agglutination; Nature of Thrombocyte Agglutinating Activity of Plasma", PSEBM, vol. 98, pp. 379–383 (1958).

Mustard et al., "Preparation of Suspensions of Washed Platelets From Humans" Brit. J. Haemat., vol. 22, pp. 193–204 (1972).

Packham et al., "Effects of Adenine Compounds on Platelet Aggregation", Am. J. Phys., vol. 17, No. 4, pp. 1009–1017 (1969).

Mason et al., "Platelet Response to Six Agglutinating Agents: Species Similarities and Differences" Experimental and Molecular Pathology, vol., 6, pp. 370–382 (1967).

Born et al., "Effects of Inorganic Ions and of Plasma Proteins on the Aggregation of Blood Platelets by Adenosine Diphosphate", J. Physiol vol. 170, pp. 397–414 (1964).

Aster et al., "Platelet Sequestration in Man. I Methods", J. of Clin. Invest., vol. 43, No. 4, pp. 843–855 (1964).

Molnar et al., "Studies on Apyreses", Arch. of Biochem. and Biophys., vol. 93, pp. 353–363 (1961).

Packham et al., "The Effect of Plasma Proteins on the Interaction of Platelets With Glass Surfaces", J. Lab. & Clin. Med., vol. 73, No. 4, pp. 686–697 (1969).

Murayama, M., Thromb Res., 33:477–85 (1984).

Bergmann I et al., Folin Haematol Int Mag Klin Morphol Blutfursch 115:869–80 (1988).

Escolar G et al., B.J. Haematology 69:379–386 (1988).

KIT FOR AN INITIAL SCREEN FOR ABNORMAL PLATELET CONDITION COMPRISING PROPYL GALLATE OR TANNIN AND A METAL ION

This is a division of application Ser. No. 08/390,273 filed on Feb. 16, 1995, now U.S. Pat. No. 5,569,590, which is a continuation of application Ser. No. 07/955,679 filed on Oct. 2, 1992, abandoned.

BACKGROUND OF THE INVENTION

The present invention resides in the field of assays to determine the capacity of blood platelets to aggregate.

Although the causes of abnormal blood clotting are many, one cause which has been of particular importance is an abnormal platelet condition which renders the platelets unable to aggregate, a phenomenon essential to normal clotting. This abnormal platelet condition can be either a deficiency in the number of platelets in the patient's blood, or a defect in the platelets.

As an example, it has been discovered that full-term pregnancy pre-eclamptic women often have prolonged bleeding times. This has been attributed to low platelet counts, and also in some instances is thought to be due to abnormalities in platelets. See, J. Ramanathan et al., Anesthesiol., 1989, 71, 188–91. Additionally, in the area of quality control, a recent article points up the need for a sensitive test which can be used to differentiate platelet concentrates which retain functional integrity after storage from those which do not, and explains that there is presently no available method for accomplishing this. T. Hervig et al., Clin. Chem., 1990, 36, No. 1, pp. 28 –31.

Prior known and used tests for screening for abnormal platelet conditions are expensive and complicated. For example, the test currently used clinically is known as a platelet aggregation test. Generally, this test is performed by using expensive reagents such as ristocetin, collagen, adenosine diphosphate, or other reagents. Since these reagents work poorly, a sensitive optical instrument is used to follow the reaction. These tests, because of their inherent insensitivity, yield little clinically useful results. Needless to say, this test is not only costly, but also time consuming. Moreover, it cannot be conducted in the physician's office, necessitating sending samples to specialized laboratories for testing.

What is therefore needed is an initial screen test for determining the capacity of a patient's platelets to aggregate which is simple, inexpensive, and which can be conducted rapidly in a physician's office. Depending on the outcome of this initial screen, further, more quantitative testing for platelet aggregation may or may not be indicated. The present invention addresses this need.

SUMMARY OF THE PREFERRED EMBODIMENT

One preferred embodiment of the invention provides an initial screen test for an abnormal platelet condition in blood. This screen comprises the steps of applying a platelet rich plasma specimen from the blood to a non-interfering test surface, contacting the platelet rich plasma specimen with an aqueous reagent including a hydroxy-substituted aromatic compound and a metal ion in sufficient concentrations to cause platelet aggregation in a normal platelet rich plasma specimen upon agitation, agitating the platelet rich plasma specimen in contact with the reagent, and visually detecting for the presence of platelet aggregates in the specimen.

Another preferred embodiment of the invention provides a kit for an initial screen for an abnormal platelet condition in blood. The kit comprises a sealed vial containing preferrably a lyophilized, or alternatively a liquid, an aqueous reagent including a hydroxy-substituted aromatic compound and a metal ion in sufficient concentrations to cause platelet aggregation in a normal platelet rich plasma specimen upon agitation; an article including a plastic or siliconized glass surface for holding a platelet rich plasma specimen from the blood; and a member for holding the vial and the article in a relationship to prevent breakage. The preferred kit also includes printed matter for instructing a user to (1) contact a platelet rich plasma specimen with the reagent, (2) agitate the specimen in contact with the reagent, and (3) visually detect for the presence of platelet aggregates in the specimen upon its agitation.

The invention provides a simple, reproducable and reliable initial screen for an abnormal platelet condition. This screen can be readily conducted in a physician's office without need for specialized equipment or prolonged sample analysis. Additional objects and advantages of the invention will be apparent from the following description.

DESCRIPTION OF THE PREFERRED EMBODIMENTS

For the purposes of promoting an understanding of the principles of the invention, reference will now be made to a preferred embodiment thereof and specific language will be used to describe the same. It will nevertheless be understood that no limitation of the scope of the invention is thereby intended, such alterations, further modifications applications of the principles of the invention being contemplated as would normally occur to one skilled in the art to which the invention pertains.

As mentioned above, one preferred embodiment of the invention relates to an initial screen for an abnormal platelet condition in blood. A platelet rich plasma specimen from the blood is applied to a non-interfering test surface. The specimen is contacted with an aqueous reagent including a hydroxy-substituted aromatic compound and a divalent metal ion. The specimen in contact with the reagent is agitated on the test surface, and a visual detection is made for the presence of platelet aggregates in the specimen.

In this regard, as used herein, the term "abnormal platelet condition" means a deficiency in the number of platelets in a blood sample or a defect in the platelets that substantially reduces or eliminates their ability to aggregate. The term "non-interfering test surface" means a surface that is inert to the platelets in the platelet rich plasma specimen and which will not itself cause them to adhere to the surface or aggregate. The term "hydroxy-substituted aromatic compound" means a compound having an aromatic ring directly attached to a hydroxyl group. The aromatic ring is preferably a carbocycle such as a phenyl ring.

The platelet rich plasma specimen may be conventionally obtained. For example, it may be obtained by centrifuging a whole blood sample so as to separate platelet rich plasma in an upper layer. The platelet rich plasma specimen may then be drawn from this upper layer. These and other facets of drawing and preparing platelet rich plasma samples for testing are well within the abilities of those of ordinary skill in the pertinent art, and need not be further detailed here.

The reagent is an aqueous medium including a hydroxy-substituted aromatic compound and a metal ion. As representative metal ions, there may be mentioned metal ions such as $Cu^{2+}$, $Ni^{2+}$, $Co^{2+}$, $Fe^{3+}$, and $Cu^+$. Among these, $Ni^{2+}$ is preferred. The metal ion is preferably included in the reagent at a level of about $10^{-9}$ to $10^{-4}$M, and more preferably about $10^{-4}$ to $10^{-5}$M. These metal ions are also preferably provided by their water soluble halogen or sulfate salts, such as cupric sulfate, nickel chloride, or cobalt chloride.

As representative hydroxy-substituted aromatic compounds, there may be mentioned ellagic acid, propyl gallate and tannin. Among these, propyl gallate is preferred. Preferably, the hydroxy-substituted aromatic compound is included in the reagent, in a molar concentration of about $10^{-2}$ to about $10^{-9}$. Where ellagic acid is used, it is more preferably included at a level of about $10^{-4}$ to about $10^{-5}$M. When propyl gallate is included, its more preferred level is about $10^{-2}$ to about $10^{-3}$M, and the more preferred level of tannin is about $10^{-5}$ to about $10^{-1}$ weight %, and even more preferably about 0.005 weight %.

In addition to the above ingredients, the reagent also preferably includes a suitable buffer to maintain physiological pH. Many acceptable buffers of this type are known, including for instance 4-(2-hydroxyethyl)- 1-piperazine-ethanesulfonic acid (also known as HEPES) and Tris (hydroxymethyl)aminomethane (also known as TRIS). The applicant's preferred buffer, however, is TRIS, which is most preferably included in a concentration of about 0.01M.

The reagent is preferably a solution. Thus, the hydroxy-substituted aromatic compound and metal ion are fully solubilized, and the activity of the reagent, or at least a substantial percentage thereof, preferably about 85% or greater, and more preferably about 90–100%, is retained even after filtering through a 0.45 micron MILLIPORE filter. Accordingly, when herein a reagent is described as being a "solution", this means that a reagent's activity is substantially the same before and after filtering, such as through a 0.45 micron MILLIPORE filter. This retention of activity is evidenced by the similar aggregation results for plasma which are obtained using the reagent before, and after filtration.

For additional information as to reagents suitable for use in this invention, reference can be made to my prior U.S. patent application, Ser. No. 07/510,178, filed Apr. 17, 1990, which is hereby incorporated herein by reference in its entirety.

The article including the non-interfering surface is preferably a plastic or siliconized test tube or a plastic or siliconized glass slide, although other suitable, economically produced articles capable of holding the plasma specimen while agitating will also be suitable. In another preferred embodiment of the invention, this article is included in a kit which also includes a vial containing the reagent, with the vial and the article being retained in a relationship to prevent breakage, such as during handling or shipping. It will be understood the such a kit can also include additional vials of reagent and/or additional articles upon which to conduct the screen, and printed matter for instructing a user of the kit as to the screening method.

In order to promote a further understanding of the invention and its preferred embodiments, the following specific Examples are provided. It will be understood that these examples are illustrative and not limiting in nature.

[A] PREPARATION OF SUITABLE REAGENTS (Also referred to as "Activators"): The following examples illustrate the preparation of reagents which are suitable for use in the screen of the invention.

EXAMPLE 1

Ellagic Acid and Copper II Activator 0.18 g tetramethylammonium hydroxide were dissolved in 1,000 ml water. 0.034 g ellagic acid were then dissolved in this tetramethylammonium hydroxide solution, whereafter 1.0 ml 0.1M cupric sulfate were added and the resulting solution mixed for 10 minutes with teflon coated stirring bar on a stir-plate. 1.2 g TRIS buffer were then dissolved into the solution. The resulting solution was clear and free from any visible particulate or other suspended matter.

EXAMPLE 2

Ellagic Acid and Nickel Activator

Example 1 was repeated except 1.0 ml 0.1M nickel chloride was used instead of the 1.0 ml 0.1M cupric sulfate to form an ellagic acid/nickel coagulation activator which was also a clear solution free from visible particulate or other suspended matter.

EXAMPLE 3

Ellagic Acid and Cobalt Activator

Example 1 was repeated except 1.0 ml 0.1M cobalt chloride was used instead of the 1.0 ml 0.1M cupric sulfate, and the TRIS buffer was not added. A clear ellagic acid/cobalt coagulation activator solution was formed. This unbuffered activator performs similarly to the buffered activators in Examples 1 and 2. The buffer further stabilizes the activators over time.

EXAMPLE 4

Propyl Gallate and Copper II Activator 0.5 g propyl gallate were dissolved in 1,000 ml water. 1.0 ml 0.1M cupric sulfate were then added, whereafter the solution was mixed for 10 minutes with teflon-coated stir bar. 1.2 g TRIS buffer were then dissolved in this solution, which was thereafter stirred for an additional 10 minutes. A propyl gallate/copper coagulation activator was formed as a clear solution without any visible suspended materials.

EXAMPLE 5

Propyl Gallate and Nickel Activator

Example 4 was repeated except 1.0 ml 0.1M nickel chloride was used instead of the cupric sulfate. A clear solution-form coagulation activator with propyl gallate and nickel was formed.

EXAMPLE 6

Propyl Gallate and Cobalt Activator

Example 4 was repeated except 1.0 ml 0.1M cobalt chloride was used the place of the cupric sulfate to form a propyl gallate/cobalt solution-form coagulation activator.

EXAMPLE 7

Tannin and Copper II Activator 0.5 g tannin were dissolved in 1,000 ml reagent water. 1.0 ml 0.1M cupric sulfate were added whereafter the resulting solution was mixed for 10 minutes with a teflon coated stirring bar on a stir-plate. Then, 1.2 g TRIS buffer were added, and the resulting solution mixed for 10 minutes with a teflon coated stir-bar. A clear solution coagulation activator with tannin and copper was thus formed containing no visible suspended matter.

EXAMPLE 8

Tannin and Nickel Activator

Example 7 was repeated except 1.0 ml 0.1M Nickel chlorine was used in the place of the cupric sulfate thus forming a solution-form coagulation activator with tannin and nickel.

EXAMPLE 9

Tannin and Cobalt Activator

Example 7 was repeated except 0.1 ml 0.1M cobalt chloride was used instead of the cupric sulfate. Also, 2.5 g HEPES hemi sodium salt were added instead of the TRIS, to thus make a coagulation activator in solution form containing tannin and cobalt.

[B] SCREENS FOR NORMAL AND ABNORMAL PLATELET CONDITION

EXAMPLES 10 [I] and 10 [II]

Screens for Abnormal Platelet Condition

[I] TESTS ON NORMAL BLOOD

Several platelet rich plasma specimens were obtained from blood known not to have an abnormal platelet condition. Each of these specimens was identically tested by placing the specimen (100 µl) on a siliconized glass slide and subsequently adding the activator of Example 5 (100 µl) to the specimen. The specimen was then agitated by gently rocking the glass slide, and tile appearance of platelet aggregates was noted. No stirring member was immersed in the fluid. (In other experiments, attempts to achieve admixture and agitation by use of a stirring member immersed in the fluid required larger sample sizes and substantially adversely affected the results.) The platelet aggregates appear as white agglomerates in the sample, and are readily detected visually. One example of a time for formation of the aggregates would be 60 seconds with normal samples. Similar results are obtained when the other activators exemplified above are employed.

[II] SCREENING OF SAMPLES HAVING ABNORMAL PLATELET CONDITION

Several screens were run on platelet rich plasma specimens known to have an abnormal platelet condition. The tests were run identically to those in Example 10 [I] above. The results show that the abnormal platelet conditions result in a failure to visually detect platelet aggregates in a period of three minutes. Similar results are obtained when the other activators illustrated in the Examples above are employed.

EXAMPLES 11–15

[I] TESTS ON NORMAL BLOOD

Instead of the propyl gallate and nickle chloride activator of Example 5, collagen, adrenalin, adenosine diphosphate, arachadonic acid, and ristocetin (each without additional metal ions) were alternately used in the procedure of Example 10 [I]. Results were much superior to mechanical platelet aggregometer tests in both time, cost, and sensitivity. However, the sensitivity was less than half that of Example 10 [I], and the tests took longer.

While the invention has been described in detail in the foregoing description, the same is to be considered as illustrative and not restrictive in character, it being understood that only the preferred embodiments have been described, and that all changes and modifications that come within the spirit of the invention are desired to be protected.

What is claimed is:

1. A kit for an initial screen for an abnormal platelet condition in blood, comprising a sealed vial containing an aqueous reagent comprising a hydroxy-substituted aromatic compound selected from the group consisting of tannin and propyl gallate and a metal ion selected from the group consisting of $Ni^{++}$, $Fe^{+++}$, $Co^{++}$, $Cu^{++}$, and $Cu^{+}$, each in a concentration sufficient to cause platelet aggregation in a normal platelet rich plasma sample upon agitation and an article comprising a plastic or siliconized glass surface for holding a plasma specimen.

2. The kit according to claim 1 further comprising a member for holding the vial and the glass article in a relationship in order to prevent breakage.

3. The kit according to claim 1 wherein the metal ion is $Ni^{++}$.

4. The kit according to claim 1 wherein the metal ion is $Cu^{+}$.

5. The kit according to claim 1 wherein the metal ion is $Cu^{++}$.

6. The kit according to claim 1 wherein the metal ion is $Co^{++}$.

7. The kit according to claim 1 wherein the metal ion is $Fe^{+++}$.

8. The kit according to claim 1 wherein the hydroxy-substituted aromatic compound is propyl gallate.

9. The kit according to claim 1 wherein the aqueous reagent comprises nickel chloride and propyl gallate.

10. The kit according to claim 1 wherein the aqueous reagent comprises cupric sulfate and propyl gallate.

11. The kit according to claim 1 wherein the aqueous reagent comprises cobolt chloride and propyl gallate.

12. The kit according to claim 1 wherein the metal ion is present in a concentration of from about $10^{-9}$ to about $10^{-4}$M.

13. The kit according to claim 1 wherein the metal ion is present in a concentration of from about $10^{-4}$ to about $10^{-5}$M.

14. The kit according to claim 1 wherein the hydroxy-substituted aromatic compound is present in a concentration of from about $10^{-2}$ to about $10^{-9}$M.

15. The kit according to claim 1 wherein the aqueous reagent further comprises a buffer to maintain physiological pH.

16. The kit according to claim 1 wherein the aqueous reagent is a solution.

* * * * *

UNITED STATES PATENT AND TRADEMARK OFFICE
CERTIFICATE OF CORRECTION

PATENT NO. : 5,637,452
DATED : 10 June 1997
INVENTOR(S) : Roy E. Speck

It is certified that error appears in the above-identified patent and that said Letters Patent is hereby corrected as shown below:

| Column | Line | |
|--------|------|---|
| 4 | 65 | Change "chlorine" to --chloride--. |

Signed and Sealed this

Twenty-fourth Day of February, 1998

Attest:

BRUCE LEHMAN

Attesting Officer

Commissioner of Patents and Trademarks